(12) United States Patent
Tada

(10) Patent No.: US 9,622,890 B2
(45) Date of Patent: Apr. 18, 2017

(54) CATHETER FOR FORMING BIOLOGICAL TISSUE HOLDING MEMBER

(71) Applicant: TERUMO KABUSHIKI KAISHA, Tokyo (JP)

(72) Inventor: Yuichi Tada, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 99 days.

(21) Appl. No.: 14/397,458

(22) PCT Filed: Apr. 24, 2013

(86) PCT No.: PCT/JP2013/062116
§ 371 (c)(1),
(2) Date: Oct. 27, 2014

(87) PCT Pub. No.: WO2013/161901
PCT Pub. Date: Oct. 31, 2013

(65) Prior Publication Data
US 2015/0094821 A1 Apr. 2, 2015

(30) Foreign Application Priority Data
Apr. 27, 2012 (JP) .................................. 2012-104149

(51) Int. Cl.
*A61F 2/06* (2013.01)
*A61F 2/945* (2013.01)
(Continued)

(52) U.S. Cl.
CPC .............. *A61F 2/945* (2013.01); *A61F 2/958* (2013.01); *A61F 2002/043* (2013.01); *A61M 2210/1032* (2013.01)

(58) Field of Classification Search
CPC .... A61F 2002/043; A61F 2/945; A61F 2/958; A61F 2002/30583; A61M 2210/1032;
(Continued)

(56) References Cited

U.S. PATENT DOCUMENTS 4,676,778 A * 6/1987 Nelson, Jr. ......... A61M 25/1011
604/101.05
5,129,883 A * 7/1992 Black ................. A61M 25/1011
604/101.03
(Continued)

FOREIGN PATENT DOCUMENTS

JP 08-155036 6/1996
JP 09-505503 6/1997
(Continued)

OTHER PUBLICATIONS

PCT Written Opinion (Japanese language) of the International Searching Authority for International Application No. PCT/JP2013/062116, dated Jul. 23, 2013, 3 pages.
(Continued)

*Primary Examiner* — Katherine M Shi
*Assistant Examiner* — Mohamed Gabr

(57) ABSTRACT

[Object]
It is an object of the present invention to provide a catheter for forming a biological tissue holding member by which a body lumen can be maintained in a dilated state even after a procedure of dilating a target part of the body lumen.
[Solution]
The catheter (100) for forming a biological tissue holding member includes: an elongated main body section (30) having a lumen (31 and 32) through which can flow a curable liquid substance that is cured in a living body; a first discharge section (10) through which the curable liquid substance supplied via the main body section is discharged in a filamentous form in a first direction intersecting the axial
(Continued)

direction of the main body section; a second discharge section (20) which is disposed on the distal side along the longitudinal direction of the main body section as compared with the first discharge section and through which the curable liquid substance supplied via the main body section is discharged in a second direction intersecting both of the axial direction and the first direction; a first rotation driving unit (16) which rotates the first discharge section in a first rotation direction; and a second rotation driving unit (24) which rotates the second discharge section in a second rotation direction reverse to the first rotation direction.

11 Claims, 9 Drawing Sheets

(51) Int. Cl.
*A61F 2/958* (2013.01)
*A61F 2/04* (2013.01)

(58) Field of Classification Search
CPC .. A61M 2025/1052; A61M 2025/1097; A61M 2025/105; A61M 2025/1015; A61M 2025/0057; A61M 2025/0073; A61M 2025/09175; A61M 2025/10; A61M 25/007; A61M 25/104; A61M 1/1072; A61M 1/1025; A61M 1/1032; A61M 1/34; A61B 17/00234; A61B 17/00491; A61B 17/12195; A61B 17/3203; A61B 17/320725; A61B 17/320758; A62C 31/05; B05B 3/06; F01C 1/20; Y10S 415/90
USPC ........................................................ 623/1.11
See application file for complete search history.

(56) References Cited

U.S. PATENT DOCUMENTS

| | | | | |
|---|---|---|---|---|
| 5,256,141 A * | 10/1993 | Gencheff | ............... | A61B 17/22 604/101.03 |
| 5,320,604 A * | 6/1994 | Walker | ............... | A61L 29/04 604/101.03 |
| 5,411,479 A * | 5/1995 | Bodden | ............... | A61M 1/3621 604/101.03 |
| 5,415,636 A * | 5/1995 | Forman | ............... | A61M 25/104 604/101.03 |
| 5,464,437 A * | 11/1995 | Reid | ............... | A61B 18/18 607/101 |
| 5,484,411 A * | 1/1996 | Inderbitzen | ............... | A61M 25/1002 604/103.08 |
| 5,505,701 A * | 4/1996 | Anaya Fernandez de Lomana | ............... | A61B 5/0422 604/101.03 |
| 5,554,119 A * | 9/1996 | Harrison | ............... | A61M 25/1002 604/101.05 |
| 5,569,197 A * | 10/1996 | Helmus | ............... | A61M 25/09 604/102.02 |
| 5,713,861 A * | 2/1998 | Vanarthos | ............... | A61M 25/0017 604/103.03 |
| 5,725,568 A * | 3/1998 | Hastings | ............... | A61L 27/56 606/191 |
| 5,868,703 A * | 2/1999 | Bertolero | ............... | A61B 90/36 604/102.01 |
| 5,919,163 A * | 7/1999 | Glickman | ............... | A61M 25/1011 604/101.05 |
| 6,749,598 B1 * | 6/2004 | Keren | ............... | A61M 1/101 604/508 |
| 6,821,265 B1 * | 11/2004 | Bertolero | ............... | A61B 90/36 604/102.03 |
| 7,048,680 B2 * | 5/2006 | Viole | ............... | A61M 1/3653 600/16 |
| 7,364,566 B2 * | 4/2008 | Elkins | ............... | A61M 25/00 604/104 |
| 7,491,163 B2 * | 2/2009 | Viole | ............... | A61M 1/3653 600/16 |
| 8,172,792 B2 * | 5/2012 | Wang | ............... | A61F 2/958 604/101.03 |
| 8,192,363 B2 * | 6/2012 | Soltani | ............... | A61N 7/022 600/439 |
| 2002/0010487 A1 * | 1/2002 | Evans | ............... | A61B 17/221 606/180 |
| 2005/0103340 A1 * | 5/2005 | Wondka | ............... | A61M 16/00 128/204.18 |
| 2006/0049276 A1 * | 3/2006 | Ivy | ............... | A62C 25/00 239/251 |
| 2006/0271150 A1 * | 11/2006 | Andreas | ............... | A61B 17/12045 623/1.11 |
| 2006/0286137 A1 * | 12/2006 | Sandhu | ............... | A61F 2/06 424/422 |
| 2007/0250050 A1 * | 10/2007 | Lafontaine | ............... | A61B 18/02 606/21 |
| 2008/0050262 A1 * | 2/2008 | Jacobsen | ............... | F01C 1/20 418/191 |
| 2010/0082012 A1 * | 4/2010 | Hattangadi | ............... | A61L 29/16 604/509 |
| 2012/0053566 A1 * | 3/2012 | Tada | ............... | A61B 17/00491 604/514 |
| 2012/0089082 A1 * | 4/2012 | Zhang | ............... | A61B 1/00135 604/22 |
| 2015/0335344 A1 * | 11/2015 | Aljuri | ............... | A61B 17/3203 606/169 |
| 2015/0343136 A1 * | 12/2015 | Nitzan | ............... | A61M 27/002 604/6.09 |

FOREIGN PATENT DOCUMENTS

| | | |
|---|---|---|
| JP | 09-505503 A | 6/1997 |
| JP | 10-510730 | 10/1998 |
| JP | 10-510730 A | 10/1998 |
| JP | 2002-345973 A | 12/2002 |
| JP | 2008-541936 A | 11/2008 |
| WO | 95/28196 A1 | 10/1995 |
| WO | 95/28796 | 10/1995 |
| WO | 96/18427 | 6/1996 |
| WO | 96/18427 A1 | 6/1996 |
| WO | 2006/130326 A2 | 12/2006 |
| WO | 2013/161901 A1 | 10/2013 |

OTHER PUBLICATIONS

English translation of PCT Written Opinion of the International Searching Authority for International Application No. PCT/JP2013/062116, dated Jul. 23, 2013, 4 pages.
Machine translation of JP2002-345973A, dated Dec. 3, 2002, 9 pages (cited above).
Machine translation of JP08-155036A, dated Jun. 18, 1996, 9 pages (cited in previously filed IDS).

* cited by examiner

FIG. 4
(A)
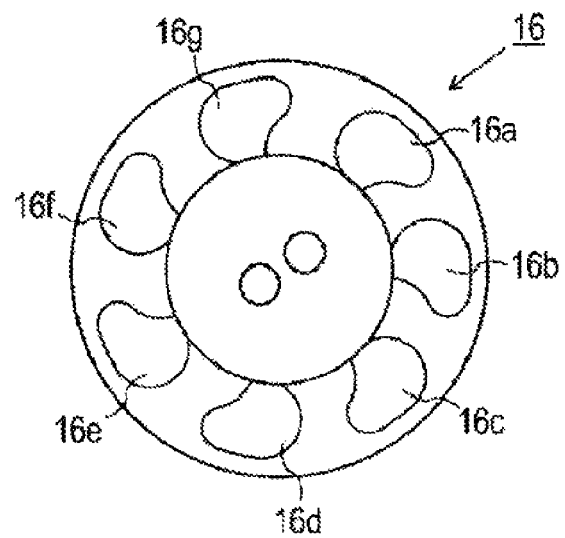
(B)
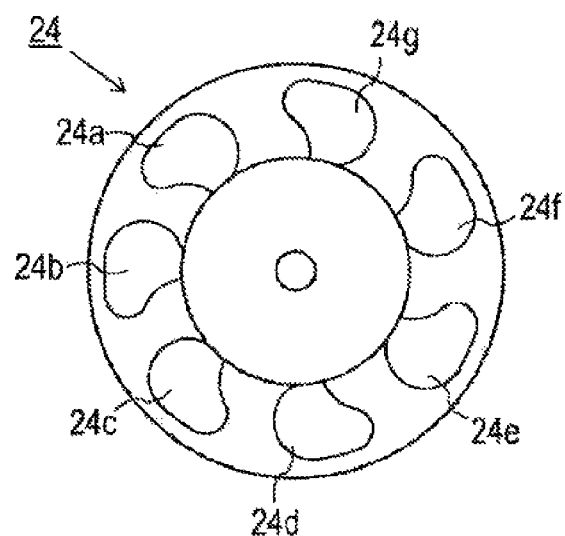

F I G . 9
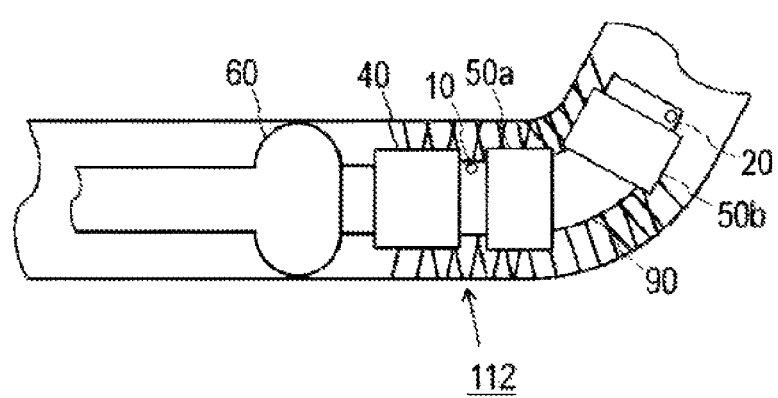

CATHETER FOR FORMING BIOLOGICAL TISSUE HOLDING MEMBER

CROSS REFERENCE TO RELATED APPLICATIONS

This application is based on International Application No. PCT/JP2013/062116, filed on Apr. 24, 2013, which claims priority to Japanese National Application No. 2012-104149, filed on Apr. 27, 2012. the entire contents of each and every foregoing application are incorporated herein by reference.

TECHNICAL FIELD

The present invention relates to a catheter for forming a biological tissue holding member that is used to form in a living body a member for holding a biological tissue.

BACKGROUND ART

In bronchial asthma and bronchomalacia, which are representative examples of respiratory system diseases, the luminal sectional area of bronchial tubes is reduced, to cause such a symptom as respiratory difficulty (dyspnea). Exemplary methods for treatment of the bronchial asthma and the like include the usage of a drug for dilating the bronchial tubes (bronchodilator) and a method of placing a stent to indwell in the bronchial tube.

In the conventional method of treatment, however, it is necessary to preliminarily measure the diameter of the lumen by use of a diagnostic imaging apparatus such as CT or an endoscope. Even if the inside diameter of the lumen could be measured, the outside diameters of commonly available stents are determined at the time of manufacture of the stents, from which a suitable one has to be chosen. Thus, it cannot be said that a stent suited to the patient's bronchial tube can always be provided.

A catheter by which the diameter of a stenosed part of a living body lumen can be freely expanded and contracted is disclosed, for example, in Patent Document 1. Specifically, Patent Document 1 discloses a technology wherein the diameter of a body lumen dilating spiral body disposed forwardly of a distal portion of a main body of a body lumen dilating catheter is freely expandable or contractible by a rotational force transmission member.

PRIOR ART DOCUMENT

Patent Document

Patent Document 1: Japanese Patent Laid-Open No. Hei 8-155036

SUMMARY OF INVENTION

Technical Problem

In the technology disclosed in Patent Document 1, the body lumen to be treated can be dilated during a procedure of dilating the body lumen. Once a catheter is drawn out of the body lumen, however, a dilating force at the target part would be lost and, as a result, the cross-sectional area of the body lumen would be reduced. Thus, there is a fear of regeneration of a dyspnea-related symptom, such as asthma.

It is an object of the present invention to provide a catheter for forming a biological tissue holding member by which a body lumen can be maintained in a dilated state even after a procedure of dilating a stenosed part (target part to be treated) of the body lumen.

Technical Solution

According to the present invention for achieving the above object, there is provided a catheter for forming a biological tissue holding member, including: an elongated main body section having a lumen through which can flow a curable liquid substance that is cured in a living body; a first discharge section through which the curable liquid substance supplied via the main body section is discharged in a filamentous form in a first direction intersecting an axial direction of the main body section; and a second discharge section which is disposed on a distal side along a longitudinal direction of the main body section as compared with the first discharge section and through which the curable liquid substance supplied via the main body section is discharged in a second direction intersecting both of the axial direction and the first direction. The catheter further includes a first rotation driving unit which rotates the first discharge section in a first rotation direction; and a second rotation driving unit which rotates the second discharge section in a second rotation direction reverse to the first rotation direction.

Advantageous Effect

In the catheter for forming a biological tissue holding member as above, the first discharge section discharges the curable liquid substance in a filamentous form in the first direction while rotating, and the second discharge section discharges the curable liquid substance in a rotation direction reverse to that of the first direction. The curable liquid substance is discharged while the catheter having the first discharge section and the second discharge section rotating in the different directions is being moved in the longitudinal direction thereof. This ensures that a layer of the curable liquid substance is formed in a mesh pattern on the internal wall surface of a body lumen, and the layer is cured after a predetermined period of time, to be a member capable of holding a biological tissue, such as a stent. Such a biological tissue holding member can be left indwelling in a living body. Evan after the catheter is drawn out, therefore, the stenosed part of the body lumen can be maintained in the dilated state. Consequently, regeneration of such a symptom as respiratory difficulty can be prevented from occurring, after the procedure of treating the stenosed part of the body lumen.

Preferably, a configuration may be adopted wherein the first rotation driving unit is provided with first rotary vanes which rotate the first discharge section by supply of the curable liquid substance to the first discharge section, and the second rotation driving unit is provided with second rotary vanes which rotate the second discharge section by supply of the curable liquid substance to the first discharge section. This configuration ensures that when a fluid is allowed to flow through the catheter, the first rotation driving unit and the second rotation driving unit are rotated, so that the first discharge section and the second discharge section discharge the curable liquid substance while rotating. Thus, it is possible, by the simple method of supplying a fluid via a main body section of the catheter, to discharge the curable liquid substance and to form therefrom a stent capable of holding a body lumen in a dilated state.

Preferably, the first discharge section is rotatably held on the main body section, and includes a first space which is disposed communicating with the lumen permitting the curable liquid substance to flow therethrough and into which the curable liquid substance is introduced via the lumen, an opening potion which communicates with the first space and which opens to a distal side of the first space, and a first discharge hole which communicates with the first space and through which the curable liquid substance is discharged. In addition, preferably, the second discharge section is rotatably held on the first discharge section, and includes a second space which is disposed communicating with the opening portion and into which the curable liquid substance is introduced from the first space, and a second discharge hole which communicates with the second space and through which the curable liquid substance is discharged. This configuration ensures that the curable liquid substance supplied via the lumen through which the curable liquid substance can flow is discharged through the first discharge hole, and is also discharged through the second discharge hole of the second discharge section after passing the opening portion. Accordingly, the curable liquid substance can be discharged in different rotation directions, without need for a structure wherein lumens are provided at two positions and in directions perpendicular to the catheter axial direction so as to supply the curable liquid substance in different rotation directions; thus, an increase in the catheter sectional area can be restrained. Consequently, the present device can be used for body lumens which are comparatively small in diameter.

Preferably, the first discharge section is provided with an opening portion lumen which extends from the opening portion and which is disposed coaxially with an axis of rotation of the first discharge section, a flexible member lower than the first discharge section and the second discharge section in rigidity is disposed between the first discharge section and the second discharge section, and the flexible member is provided with a second space communication lumen which communicates with the second space in the second discharge section. In this case, the catheter discharges the curable liquid substance while being deformed along the shape of a body lumen owing to the presence of the flexible member, to thereby form a biological tissue holding member. Therefore, the biological tissue holding member such as a stent can be easily formed, even in the case where the body lumen is curved or bent so that it is difficult for the catheter to enter into the body lumen.

Preferably, a configuration may be adopted wherein an expansion catheter is provided with an expandable expansion member supporting a living body lumen at the time of forming the biological tissue holding member, the supporting being conducted on a distal side as compared with the second discharge section of the catheter for forming a biological tissue holding member. In this case, the biological tissue holding member is formed in a state where a stenosed part of a blood vessel or the like is dilated. Therefore, the biological tissue holding member can be formed in the state of dilating the stenosed part. Accordingly, such a symptom as respiratory difficulty can be improved assuredly.

Preferably, a configuration may be adopted wherein the expansion catheter has an expansion passing lumen in which the catheter for forming a biological tissue holding member is movably passed. This configuration ensures that the curable liquid substance is discharged while the catheter for forming a biological tissue holding member is being moved in the longitudinal direction thereof, whereby the biological tissue holding member is formed. Therefore, the biological tissue holding member formed from the curable liquid substance can be controlled in its length to a desired longitudinal length.

Preferably, a configuration may be adopted wherein the expansion catheter includes a balloon catheter provided with an expansion balloon as the expansion member. This permits the expansion catheter to be expanded by inflating the expansion balloon by use of an indeflator or the like. Therefore, a biological tissue holding member formed from the curable liquid substance can be easily formed in a stenosed part of a body lumen, without need for any special apparatus for expanding the expansion catheter.

Preferably, a configuration may be adopted wherein a holding balloon by which the catheter for forming a biological tissue holding member is held on a proximal side as compared with the first discharge section of the catheter for forming a biological tissue holding member while being positioned with respect to the radial direction of a living body lumen. In this case, the catheter for forming a biological tissue holding member discharges the curable liquid substance while in the state of being fixed in a predetermined position in a living body, thereby forming the biological tissue holding member. Therefore, it is possible to prevent the catheter from being moved in the longitudinal direction thereof due to a discharge pressure at which the curable liquid substance is discharged. Besides, it is possible to prevent the discharge direction of the first discharge section or the second discharge section from deviating from a desired direction. Consequently, a biological tissue holding member can be formed in a stenosed part of a body lumen in a stable manner.

BRIEF DESCRIPTION OF DRAWINGS

FIG. 4(A) is a plan view showing a first discharge section as viewed from the proximal side of the catheter, whereas FIG. 4(B) is a plan view of a second discharge section as viewed from the proximal side of the catheter.

FIG. 9 illustrates a state where the catheter assembly is inserted in a living body lumen.

MODES FOR CARRYING OUT THE INVENTION

Figure 1:
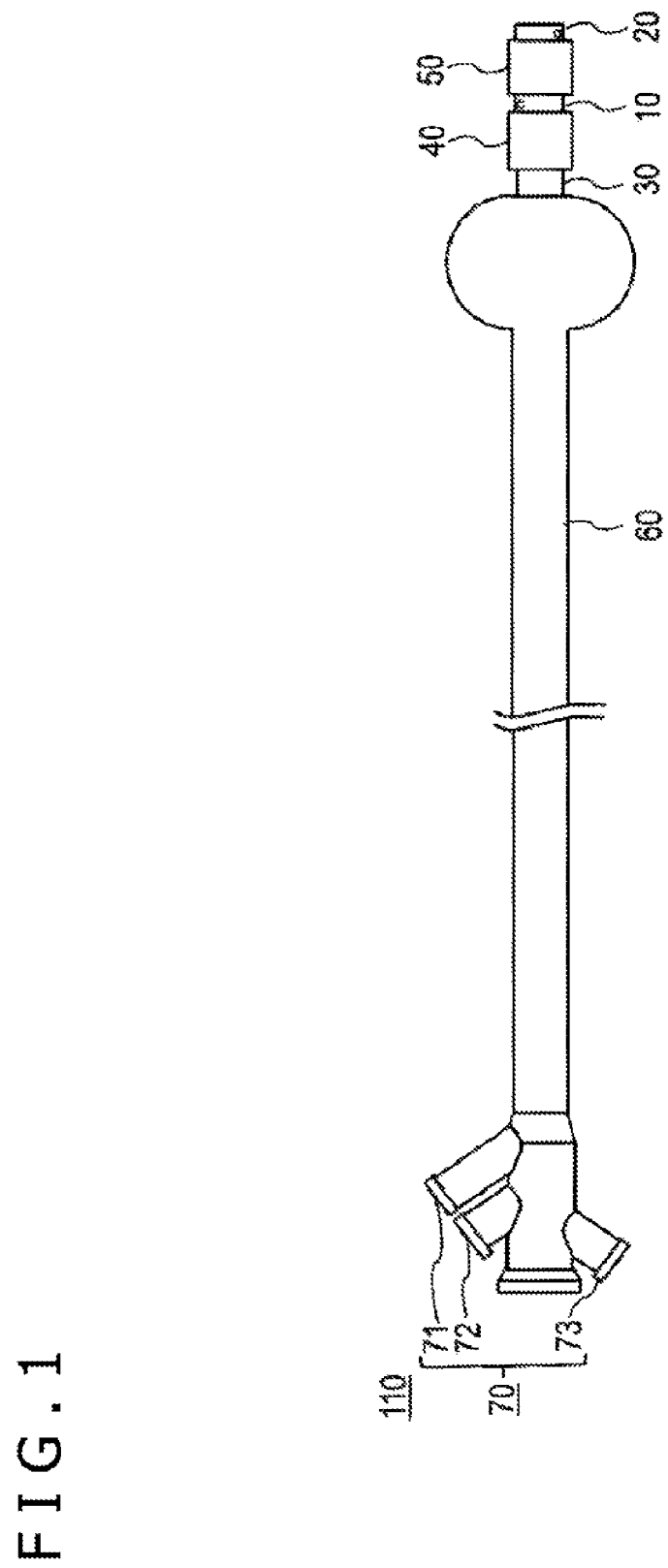
FIG. 1 shows an external appearance of a catheter assembly having a catheter for forming a biological tissue holding member according to a first embodiment of the present invention.

Some embodiments of the present invention will now be described below, referring to the accompanying drawings. Note that the following description is not to limit the technical scope described in the appended claims or the significance of the terms used in the claims. In addition, the dimensional ratios in the drawings may be exaggerated for convenience of explanation and, therefore, be different from the actual ratios.

[First Embodiment]

Figure 2:
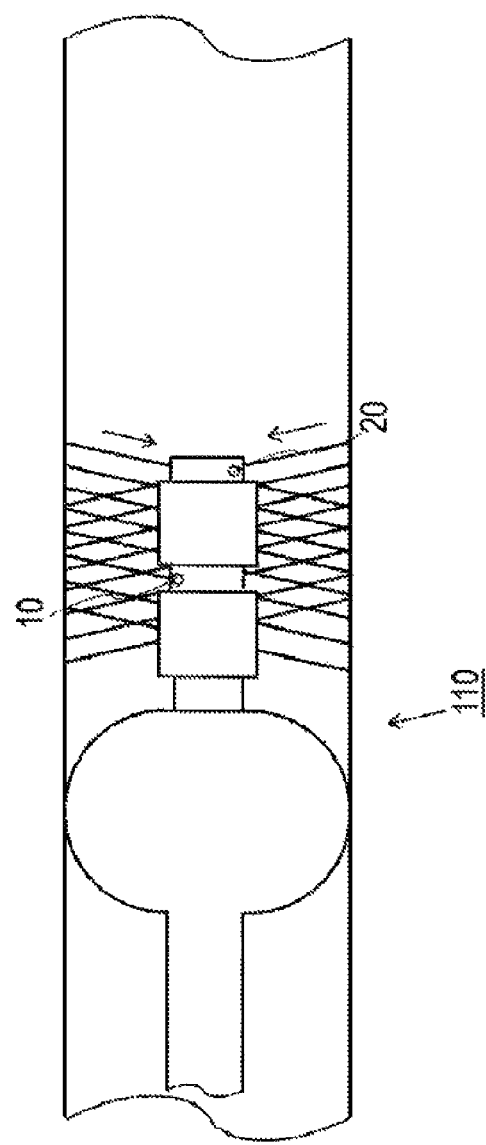
FIG. 2 illustrates a state where the catheter assembly is inserted in a living body lumen.
Figure 3:
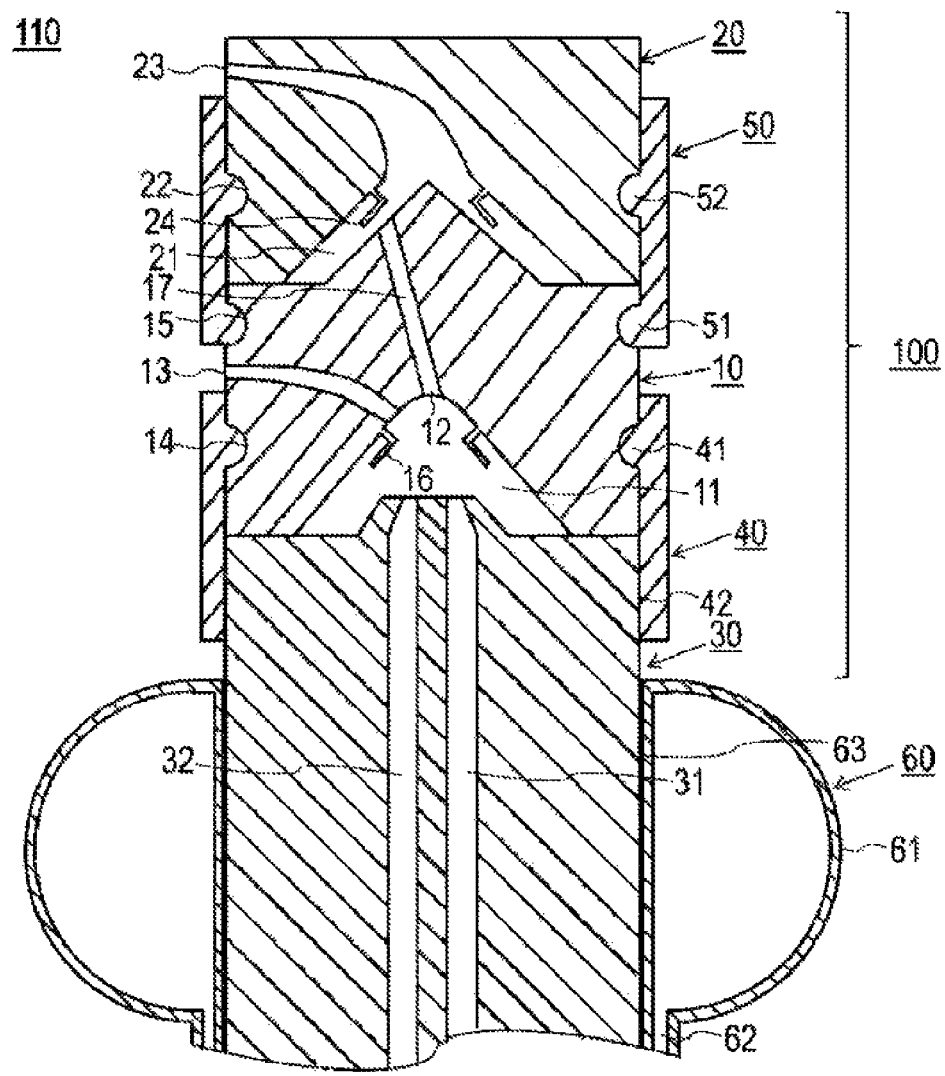
FIG. 3 is a sectional view showing a distal portion of the catheter assembly.

FIG. 1 shows an external appearance of a catheter assembly having a catheter for forming a biological tissue holding member according to a first embodiment of the present invention; FIG. 2 illustrates a state where the catheter assembly is inserted in a living body lumen; FIG. 3 is a sectional view showing a distal portion of the catheter assembly; and FIG. 4(A) is a plan view showing a first discharge section as viewed from the proximal side of the catheter, whereas FIG. 4(B) is a plan view showing a second discharge section as viewed from the proximal side of the catheter.

Referring to FIGS. 1 and 2, a catheter 100 for forming a biological tissue holding member according to the first embodiment includes: an elongated main body section 30 having lumens 31 and 32 through which curable liquid substances can flow; a first discharge section 10 through which a mixture of the curable liquid substances supplied via the main body section 30 and to be cured in a living body is discharged in a filamentous form in a first direction intersecting the axial direction of the main body section 30; and a second discharge section 20 which is disposed on a distal side along the longitudinal direction of the main body section 30 as compared with the first discharge section 10 and through which the mixture of the curable liquid substances supplied via the main body section 30 is discharged in a second direction intersecting both of the axial direction and the first direction.

In addition, the catheter 100 for forming a biological tissue holding member includes: a first rotation driving unit 16 which rotates the first discharge section 10 in a first rotation direction; and a second rotation driving unit 24 which rotates the second discharge section 20 in a second rotation direction reverse to the first rotation direction. A hub 70 is firmly attached to the proximal side of the main body section 30. To the distal end of the main body section 30 is joined a rotation holding section 40 which rotatably holds the first discharge section 10. Besides, the second discharge section 20 is rotatably held by an interlock member 50 provided on the distal side of the first discharge section 10.

A holding balloon 60 for holding in a living body lumen the catheter 100 for forming a biological tissue holding member is provided on an outside surface of the main body section 30 on the proximal side as compared with the first discharge section 10. The catheter 100 and the holding balloon 60 constitute a catheter assembly 110. The catheter 100 for forming a biological tissue holding member is introduced via a pharynx or the like, and is delivered into a body lumen such as a blood vessel or the trachea, to be used there. Now, a detailed description will be made below.

As shown in FIG. 1, the hub 70 is formed with: curable liquid substance introduction ports 71 and 72 for introducing curable liquid substances from the proximal side; and a holding fluid pressure feeding port 73 for pressure feeding of a fluid into the holding balloon 60 provided on the proximal side as compared with the discharge sections 10 and 20 so that the catheter 100 can be held in a living body lumen. The introduction of the curable liquid substances and the holding fluid is conducted by putting suction pressure feeding means (not shown) such as an indeflator or a pump in communication with the hub 70. Examples of the material constituting the hub 70 include, but are not limited to, thermoplastic resins such as polycarbonate, polyamide, polysulfone, polyallylate, and methacrylate-butylene-styrene copolymer.

The first discharge section 10 includes: a first space 11 which is disposed communicating with the curable liquid substance lumens 31 and 32 and into which the curable liquid substances are introduced via the curable liquid substance lumens 31 and 32; an opening portion 12 which communicates with the first space 11 and which opens to the distal side of the first space 11; an opening portion lumen 17 through which the mixture of the curable liquid substances flows from the opening portion 12 toward the second discharge section 20; and a first discharge hole 13 which communicates with the first space 11 and through which the mixture of the curable liquid substances is discharged. In addition, the first discharge section 10 is provided with a first engaging part 14 which engages the rotation holding section 40 so as to rotatably hold the first discharge section 10, and with a second engaging part 15 which engages the interlock member 50 interlocking the first discharge section 10 and the second discharge section 20 to each other. Furthermore, the first discharge section 10 is provided with the first rotation driving unit 16 which rotates the first discharge section 10.

The first engaging part 14 engages an engaging part 41 of the rotation holding section 40 so as to rotatably hold the first discharge section 10. The engaging part 41 of the rotation holding section 40 is formed to be semicircular and convexed in sectional shape, and, correspondingly to this, the first engaging part 14 is formed by being cut out in a semicircular and concaved sectional shape. The second engaging part 15 is an engaging part for engagement with an engaging part 51 of the interlock member 50, and is formed in a semicircular and concaved sectional shape, like the first engaging part 14.

The first space 11 is a roughly conical cavity portion on the proximal side in the first discharge section 10. The curable liquid substances discharged via the curable liquid substance lumens 31 and 32 are mixed with each other in the first space 11, and the resulting mixture is discharged to a desired part in a living body, to be cured there.

The first rotation driving unit 16 is composed of first rotary vanes 16a to 16g joined to a conical side surface, or one of wall surfaces defining the first space 11 in the first discharge section 10, as shown in FIG. 4(A). The curable liquid substances supplied via the curable liquid substance lumens 31 and 32 pass the first rotary vanes 16a to 16g, which are joined to the wall surface of the first space 11, to flow into the opening portion 12, while displacing the first rotary vanes 16a to 16g in the rotation direction, whereby the first discharge section 10 is rotated. The first rotary vanes 16a to 16g are so formed as to be rotated counterclockwise, as the catheter 100 is viewed from the proximal side.

Through the first discharge hole 13, the mixture formed in the first space 11 from the curable liquid substances flowing down the first space 11 is discharged to the outside of the catheter 100. The first discharge section 10 discharges the mixture of the curable liquid substances while being rotated counterclockwise, as the catheter 100 is viewed from the proximal side, by the first rotary vanes 16a to 16g. Here, the first direction in which the mixture of the curable liquid substances is discharged from the first discharge section 10 is an angular direction that is different from the longitudinal direction of the catheter 100 and that intersects the longitudinal direction. The first direction is determined according to the sizes of the lumens via which the curable liquid substances are discharged, the diameter of the first discharge hole 13, and the physical properties of the curable liquid substances.

The opening portion 12 is formed on the rear side of the wall surface of the first space 11. The opening portion lumen 17 is a lumen, circular in section, for delivering the mixture of the curable liquid substances to the second discharge section 20. The quantities of fluid discharged to the first discharge section 10 and the second discharge section 20 are controlled by regulating the inside diameters of the first discharge hole 13 and the opening portion 12 and/or the inclination angles of the first discharge hole 13 and the opening portion 12 in relation to the axis of rotation. The opening portion lumen 17 pierces to the distal side of the first discharge section 10, and guides to the second discharge section 20 the mixture of the curable liquid substances flowing thereinto via the opening portion 12. The shape of the first discharge section 10 on the distal side is formed to be conical, in conformity with the shape of the second discharge section 20 on the proximal side, and an outlet of the opening portion lumen 17 is formed in the conical side surface.

The second discharge section 20 is provided with: a second space 21 which is disposed communicating with the opening portion 12 and into which the mixture of the curable liquid substances is introduced from the first space 11; an engaging part 22 which engages the interlock member 50 that rotatably holds the second discharge section 20; and a second discharge hole 23 which communicates with the second space 21 and through which the mixture of the curable liquid substances is discharged. In addition, second rotary vanes 24a to 24g are joined to a side surface of the second space 21, as the second rotation driving unit 24 for rotating the second discharge section 20. Note that the engaging part 22 is the same as the engaging parts 14 and 15 in configuration, and, therefore, a description thereof is omitted.

The second space 21 is defined by a conically shaped side surface, like the first space 11. The mixture of the curable liquid substances flowing down the opening portion lumen 17 is discharged toward the second rotary vanes 24a to 24g disposed in the second space 21, to thereby rotate the second discharge section 20.

Like the first rotary vanes 16a to 16g, the second rotary vanes 24a to 24g are joined to the conical side surface of the second space 21, and rotate the second discharge section 20 as the mixture of the curable liquid substances supplied via the opening portion 12 passes the second rotary vanes 24a to 24g. As shown in FIG. 4(B), the second rotary vanes 24a to 24g are provided in such an orientation as to be rotated clockwise as viewed from the proximal side. This ensures that the second discharge section 20 is rotated clockwise as viewed from the proximal side.

The second discharge hole 23 intersects the longitudinal direction of the main body section 30, like the first discharge hole 13; furthermore, the second discharge hole 23 serves to discharge the mixture of the curable liquid substances in a direction intersecting the first direction in which the filamentous plugging matter is discharged from the first discharge hole 13. Since the second discharge section 20 is rotated by the second rotary vanes 24a to 24g in a direction reverse to the rotation direction of the first discharge section 10 and the second discharge hole 23 discharges the mixture of the curable liquid substances in a direction intersecting the longitudinal direction, the second discharge hole 23 serves to discharge the mixture of the curable liquid substances in the second direction which intersects the first direction. With the two sets of rotary vanes thus configured to be different in vane orientation, it is ensured that the first discharge section 10 and the second discharge section 20 are rotated in different directions, whereby the mixture of the curable liquid substances can be discharged in different directions.

The main body section 30 has the curable liquid substance lumens 31 and 32 through which to introduce the two kinds of curable liquid substances. The curable liquid substance lumens 31 and 32 communicate with the curable liquid substance introduction ports 71 and 72. In order to discharge the mixture of the curable liquid substances, two kinds of reactant liquids are introduced into the lumens 31 and 32, and the curable liquid substances are mixed with each other in the first space 11 in the first discharge section 10. Examples of the curable liquid substances include a cyanoacrylate-based adhesive.

The rotation holding section 40 includes a hollow tubular body which is formed to be greater than the main body section 30 in outside diameter and which is joined to a distal portion of the main body section 30. The rotation holding section 40 is provided with the engaging part 41 which engages the first engaging part 14 of the first discharge section 10 so as to rotatably support the first discharge section 10, and with a joint part 42 which is joined to the main body section 30.

The engaging part 41 is formed in a semicircular convexed sectional shape, which corresponds to the structure wherein the first engaging part 14 of the first discharge section 10 is formed in a semicircular and concaved shape in section. The joint part 42 is joined on the proximal side of the rotation holding section 40 by thermal welding, but this is not restrictive; for example, the joining may be effected by soldering, brazing, adhesion with an adhesive, or the like.

The interlock member 50 is a member for rotatably holding the second discharge section 20. The interlock member 50 has the engaging part 51 which engages the second engaging part 15 of the first discharge section 10, and an engaging part 52 which engages the engaging part 22 of the second discharge section 20. The engaging parts 51 and 52 are the same as the engaging part 41 in configuration, and, therefore, a description thereof is omitted here.

The holding balloon 60 is provided proximally of the first discharge section 10, and is mounted on an outside surface of the main body section 30 so that the catheter 100 can be moved in the longitudinal direction. The holding balloon 60 includes: a balloon part 61 for holding the catheter 100 while positioning the catheter 100 in the radial direction of a living body lumen; a holding fluid lumen 62 for expansion of the balloon part 61; and a catheter-passing lumen 63 in or through which the catheter 100 is passed movably in the longitudinal direction.

The balloon part 61 is formed from a material which can be flexibly deformed inside a body lumen so as to stably discharge the mixture of the curable liquid substances toward wall surfaces in the body lumen. Examples of the material include silicone rubber, latex, such polymers as polyamide, polyethylene terephthalate, etc., elastomer materials, and so on. The holding fluid lumen 62 is a lumen for delivery to the balloon part 61 of an expansion fluid (e.g., nitrogen gas) for expanding the balloon part 61, and communicates with the holding fluid pressure feeding port 73 at a proximal portion thereof.

The catheter-passing lumen 63 is so formed that the catheter 100 can be moved in the longitudinal direction in a state where the holding balloon 60 is held in a predetermined position in a living body lumen.

Hereafter, description will be made of a procedure of forming a biological tissue holding member in a stenosed part of a body lumen, such as a blood vessel or a bronchial tube, by use of the catheter assembly having the catheter for forming a biological tissue holding member according to this embodiment.

First, the catheter assembly 110, with the holding balloon 60 in a deflated state, is inserted into a body lumen by way of a mouth or a nose. It is preferable for the insertion of the catheter assembly 110 to be carried out under radioscopy, in view of enhanced visual checking properties. In this instance, the catheter assembly 110 may be guided into the vicinity of a target part by use of a bronchoscope.

When it can be confirmed that the catheter assembly 110 has reached a body lumen where to form a biological tissue holding member such as a stent, a fluid is fed under pressure into the balloon part 61 of the holding balloon 60 by use of an indeflator or the like, to inflate the balloon part 61, thereby fixing the holding balloon 60 inside the body lumen. Then, a cyanoacrylate-based adhesive is introduced via the curable liquid substance introduction ports 71 and 72. The curable liquid substances are mixed with each other in the first space 11, and the resulting mixture rotates the first rotary vanes 16a to 16g, whereby the first discharge section 10 is rotated and the mixture is discharged via the first discharge hole 13.

The mixture of the curable liquid substances having passed the opening portion lumen 17 passes the second space 21 in the second discharge section 20, while rotating the second rotary vanes 24a to 24g, whereby the second discharge section 20 is rotated in a direction reverse to the rotation direction of the first discharge section 10. The catheter 100 for forming a biological tissue holding member is movable in the longitudinal direction along the internal wall surface of the holding balloon 60. When the catheter 100 for forming a biological tissue holding member is moved in the longitudinal direction by the operator, therefore, the mixture of the curable liquid substances is discharged obliquely, as shown in FIG. 2. The first discharge section 10 and the second discharge section 20 serve to discharge the mixture of the curable liquid substances toward the internal wall surface of the body lumen while rotating in the different rotation directions, whereby a layer of the mixture of the curable liquid substances is formed in a mesh pattern on the internal wall surface. The mixture of the curable liquid substances thus adhered to the inner wall surface of the body lumen is left to stand for a predetermined period of time, to be thereby cured to form a biological tissue holding member such as a stent. Owing to the inflation of the holding balloon 60, the biological tissue holding member is formed in a size conforming to the individual body lumen of the patient. Besides, the biological tissue holding member exhibits a tension even after the procedure. Accordingly, a sense of respiratory difficulty (dyspnea) in such a symptom as bronchomalacia can be improved by the catheter 100, even after the procedure.

As has been described above, the catheter 100 for forming the biological tissue holding member according to the first embodiment includes: the main body section 30 having the lumens 31 and 32 for the curable liquid substances curable in a living body; and the first discharge section 10 by which the mixture of the curable liquid substances supplied from the main body section 30 is discharged in a filamentous form in the first direction intersecting the axial direction of the main body section 30. In addition, the catheter 100 for forming a biological tissue holding member includes the second discharge section 20 which is disposed distally of the first discharge section 10 and by which the mixture of the curable liquid substances supplied from the main body section 30 is discharged in the second direction intersecting both of the axial direction and the first direction. Furthermore, the catheter 100 is provided with the first rotation driving unit 16 which rotates the first discharge section 10 in the first rotation direction, and the second rotation driving unit 24 which rotates the second discharge section 20 in the second rotation direction.

The first discharge section 10 and the second discharge section 20 discharge the mixture of the curable liquid substances while rotating in the different directions. With the catheter 100 moved in the longitudinal direction of the body lumen, therefore, a layer of the mixture of the curable liquid substances can be formed in a mesh pattern on the internal wall surface of the body lumen. By leaving the layer of the mixture of the curable liquid substances to stand for a predetermined period of time so as to cure the mixture, therefore, it is possible to form a biological tissue holding member, such as a stent. In addition, even after the procedure of treating the stenosed part of the body lumen, it is possible to hold the body lumen in the dilated state.

In addition, the first rotation driving unit 16 has the first rotary vanes 16a to 16g which rotate the first discharge section 10 by the supply of the curable liquid substances, and the second rotation driving unit 24 has the second rotary vanes 24a to 24g which rotate the second discharge section 20 by the supply of the mixture of the curable liquid substances to the second discharge section 20. Therefore, by only causing the curable liquid substances to flow through the catheter 100, the first rotation driving unit 16 and the second rotation driving unit 24 can be easily rotated, to discharge the mixture of the curable liquid substances, thereby forming the biological tissue holding member such as a stent.

Besides, the first discharge section 10 is rotatably held on the main body section 30, and includes: the first space 11 which is disposed communicating with the curable liquid substance lumens 31 and 32 permitting the curable liquid substances to flow therethrough and into which the curable liquid substances are supplied via the curable liquid substance lumens 31 and 32; the opening portion 12 which communicates with the first space 11 and which opens to the distal side of the first space 11; and the first discharge hole 13 which communicates with the first space 11 and through which the mixture of the curable liquid substances is discharged. The second discharge section 20 is rotatably held on the first discharge section 10, and includes: the second space 21 which is disposed communicating with the opening portion 12 and into which the mixture of the curable liquid substances is introduced from the first space 11; and the second discharge hole 23 which communicates with the second space 21 and through which the mixture of the curable liquid substances is discharged. Therefore, the curable liquid substances supplied via the curable liquid substance lumens 31 and 32 are discharged through the first discharge hole 13, and is also discharged through the second discharge hole 23 after passing the opening portion 12. Accordingly, the mixture of the curable liquid substances can be discharged in different directions, without need for a structure wherein lumens are provided at two positions and in directions perpendicular to the catheter axial direction so as to discharge the mixture of the curable liquid substances in different directions; thus, an increase in the catheter sectional area can be restrained. Consequently, the present device (catheter assembly 110) can be used for body lumens which are comparatively small in diameter.

In addition, the catheter-passing lumen 63 permitting the catheter 100 to move therein or therethrough and the holding balloon 60 for holding the catheter 100 while positioning the catheter 100 in the radial direction of a living body lumen are provided on the proximal side relative to the first discharge section 10 of the catheter 100. Therefore, the catheter assembly 110 having the holding balloon 60, in the state of being held in a predetermined position in a living body lumen, discharges the mixture of the curable liquid substances so as to form therefrom a biological tissue holding member. Accordingly, it is possible to prevent the catheter from being moved in the longitudinal direction thereof due to a discharge pressure at which the mixture of the curable liquid substances is discharged. Also, it is possible to prevent the discharge direction of the first discharge section 10 or the second discharge section 20 from deviating from a desired direction. Consequently, a biological tissue holding member can be formed in a stenosed part of a body lumen in a stable manner.

[Second Embodiment]

Figure 5:
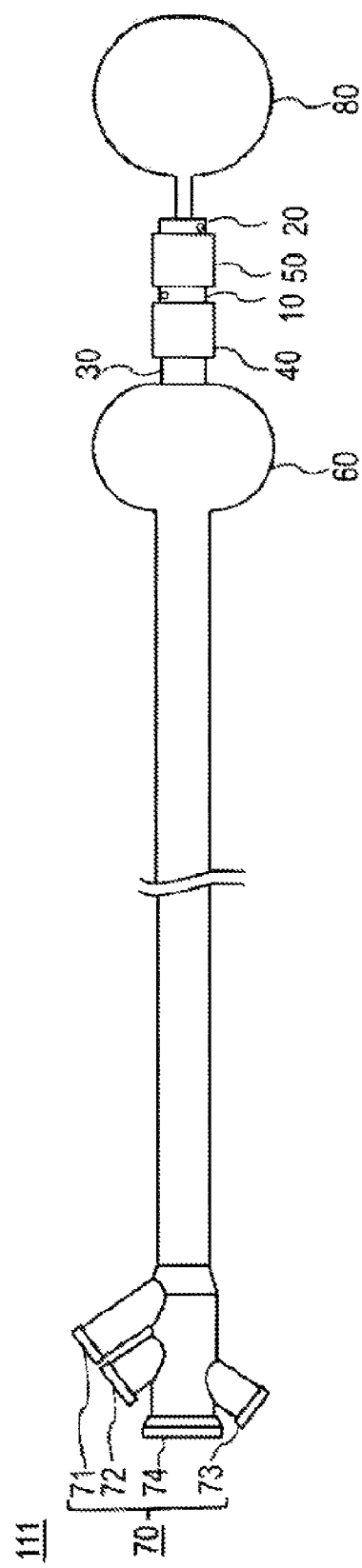
FIG. 5 shows an external appearance of a catheter assembly having a catheter for forming a biological tissue holding member according to a second embodiment of the present invention.
Figure 6:
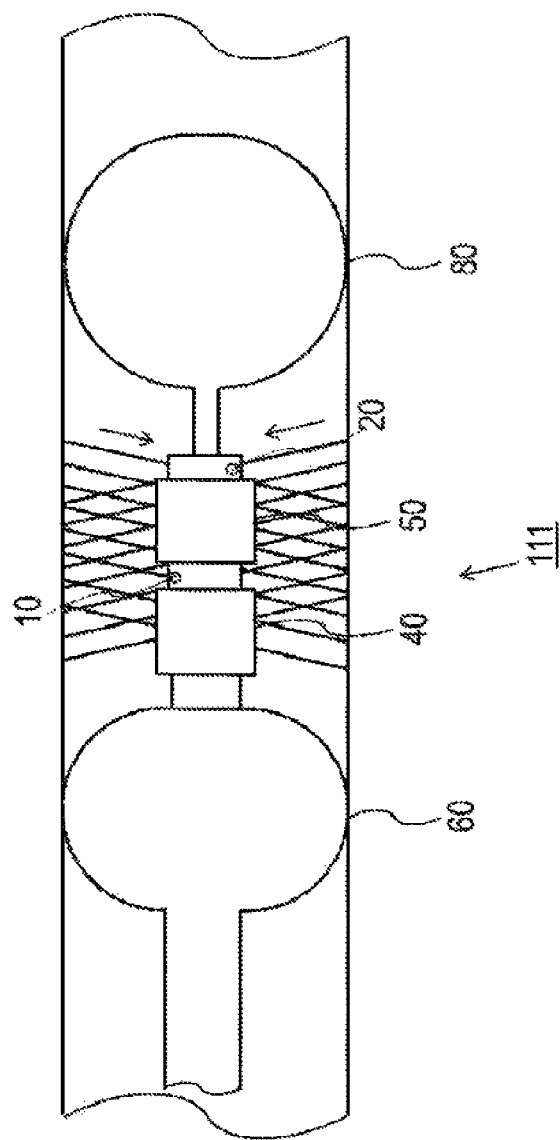
FIG. 6 illustrates a state where the catheter assembly is inserted in a living body lumen.
Figure 7:
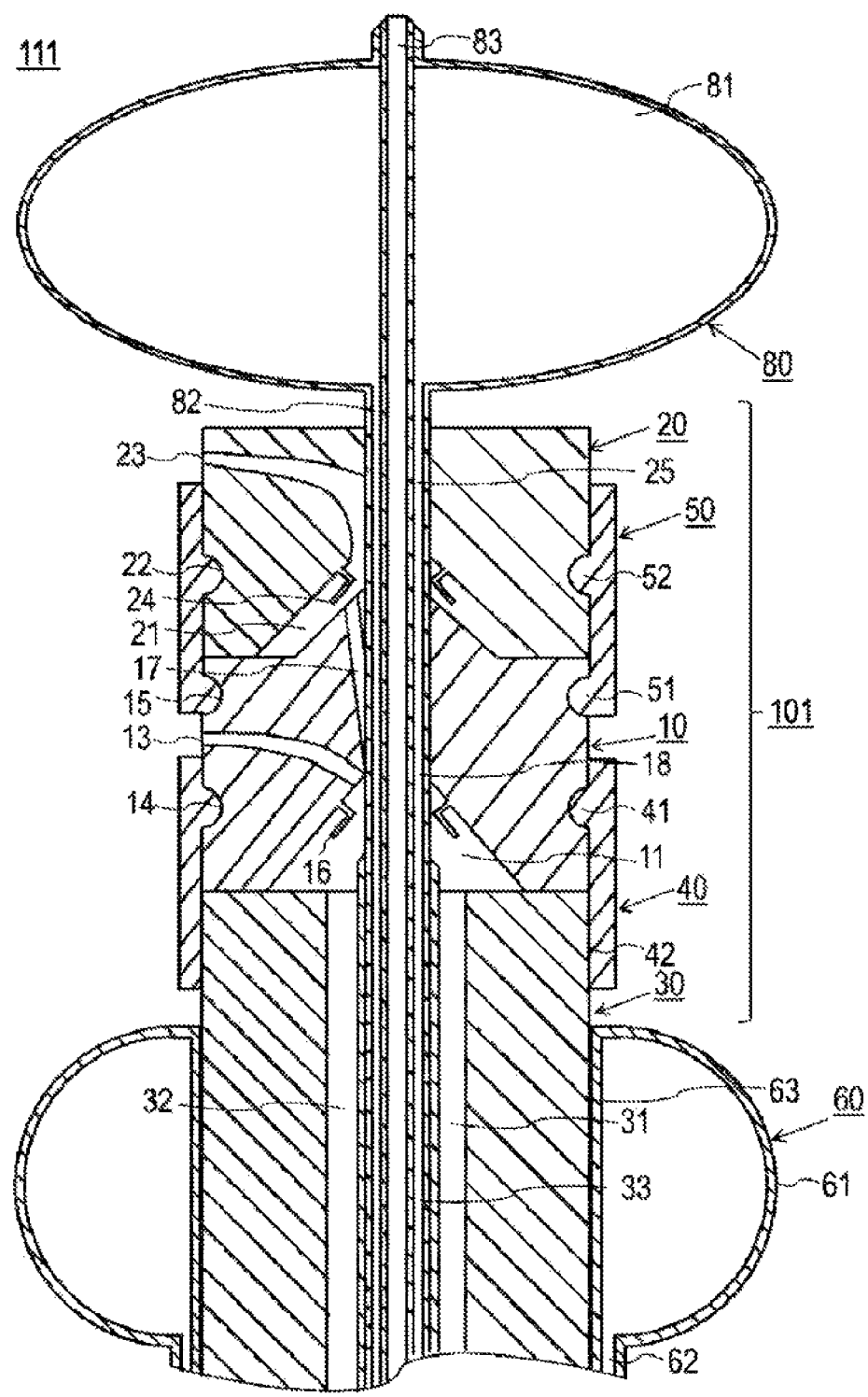
FIG. 7 is a sectional view showing a distal portion of the catheter assembly.

FIG. 5 shows an external appearance of a catheter assembly having a catheter for forming a biological tissue holding member according to a second embodiment; FIG. 6 illustrates a state where the catheter assembly is inserted in a living body lumen; and FIG. 7 is a sectional view showing a distal portion of the catheter assembly. Note that the same configurations as those in the first embodiment above are denoted by the same reference numerals as used above, and descriptions thereof will be omitted.

In the first embodiment above, description has been made of an exemplary configuration wherein the holding balloon holds the catheter in a predetermined position in a body lumen, for which a biological tissue holding member is to be formed, on the proximal side with respect to the body lumen so as to hold the size of the body lumen. However, a configuration as follows may be adopted for holding a stenosed part of a body lumen in a dilated state.

In the second embodiment, a catheter assembly 111 is provided, in addition to a holding balloon 60, with an expansion balloon 80 for expanding a body lumen to a predetermined size. The expansion balloon 80 is provided on the distal side relative to a second discharge section 20 of a catheter 101. A first discharge section 10, the second discharge section 20, and a main body section 30 constituting the catheter 101 are provided respectively with expansion balloon passing lumens 18, 25, and 33 for passing the expansion balloon 80 therethrough. In this embodiment, besides, a hub 70 is provided with a guide wire passing port 74 for passing a guide wire therethrough.

The expansion balloon 80 includes: a balloon part 81 for expanding a body lumen to a predetermined size; an expansion fluid lumen 82 which communicates with the balloon part 81 for pressure feeding of a fluid such as nitrogen gas into the balloon part 81; and a guide wire passing lumen 83 in which the guide wire is inserted precedently to the insertion of the catheter. The balloon part 81 and the expansion fluid lumen 82 of the expansion balloon 80 are the same in configuration as the balloon part 61 and the holding fluid lumen 62 of the holding balloon 60 described above, and, therefore, descriptions of them are omitted here.

The guide wire passing lumen 83 communicates with the guide wire passing port 74, and is formed so as to deliver the catheter 101 to a stent-forming site in a body lumen.

Hereafter, description will be made of a procedure of forming a biological tissue holding member inside a body lumen by use of the catheter for forming a biological tissue holding member according to the second embodiment. First, in a state where a guide wire is set extending through the catheter assembly 111, the guide wire is precedingly delivered into the body lumen, such as a bronchial tube, via a pharynx or the like.

Next, the catheter assembly 111 is inserted along the guide wire to a biological tissue holding member forming site. When the arrival of the catheter assembly 111 in the site is confirmed, the guide wire is drawn out.

Subsequently, a fluid such as nitrogen gas is fed under pressure into the holding balloon 60 and the expansion balloon 80 by use of suction pressure-feeding means, to inflate the holding balloon 60 and the expansion balloon 80, whereby the vicinity of a site at which to form a biological tissue holding member such as a stent is expanded to and held at a predetermined size. Then, curable liquid substances are fed under pressure through curable liquid substance lumens 31 and 32, are mixed with each other in a first space 11, and the resulting mixture is discharged through a first discharge hole 13 and a second discharge hole 23 while moving the catheter 101 in the longitudinal direction of the body lumen. While the dilated size of the body lumen can be held by use of the holding balloon 60 alone, the use of the expansion balloon 80 makes it possible to hold the size of the body lumen also on the distal side of the catheter assembly 111. This enables the size of the biological tissue holding member to be conditioned at a higher accuracy along the axial direction of the body lumen. Consequently, such a symptom as respiratory difficulty (dyspnea) can be reliably improved.

As aforementioned, the catheter assembly 111 having the catheter 101 for forming a biological tissue holding member according to the second embodiment is configured to possess the inflatable expansion balloon 80 for supporting the body lumen on the distal side as compared with the second discharge section 20. Therefore, the size of the biological tissue holding member can be controlled by the expansion balloon 80, even on the distal side in relation to the site in which the catheter assembly 111 is inserted. Consequently, it is possible to further enhance the accuracy of the diameter of the biological tissue holding member along the axial direction, and to securely improve such a symptom as respiratory difficulty.

In addition, the catheter assembly 111 is provided with the expansion balloon passing lumens 18, 25, and 33 so that the catheter 101 can move the expansion balloon 80. Therefore, the mixture of the curable liquid substances can be discharged while the catheter 101 is being moved, as desired, within the body lumen located between the expansion balloon 80 and the holding balloon 60. This enables the formation, in the body lumen, of a biological tissue holding member such as a stent with a diameter controlled highly accurately along the axial direction.

Besides, in this embodiment, the body lumen is expanded by the holding balloon 60. Therefore, a biological tissue holding member such as a stent can be easily formed inside a body lumen, by a method of feeding an expansion fluid under pressure, and without using any special apparatus.

[Third Embodiment]

Figure 8:
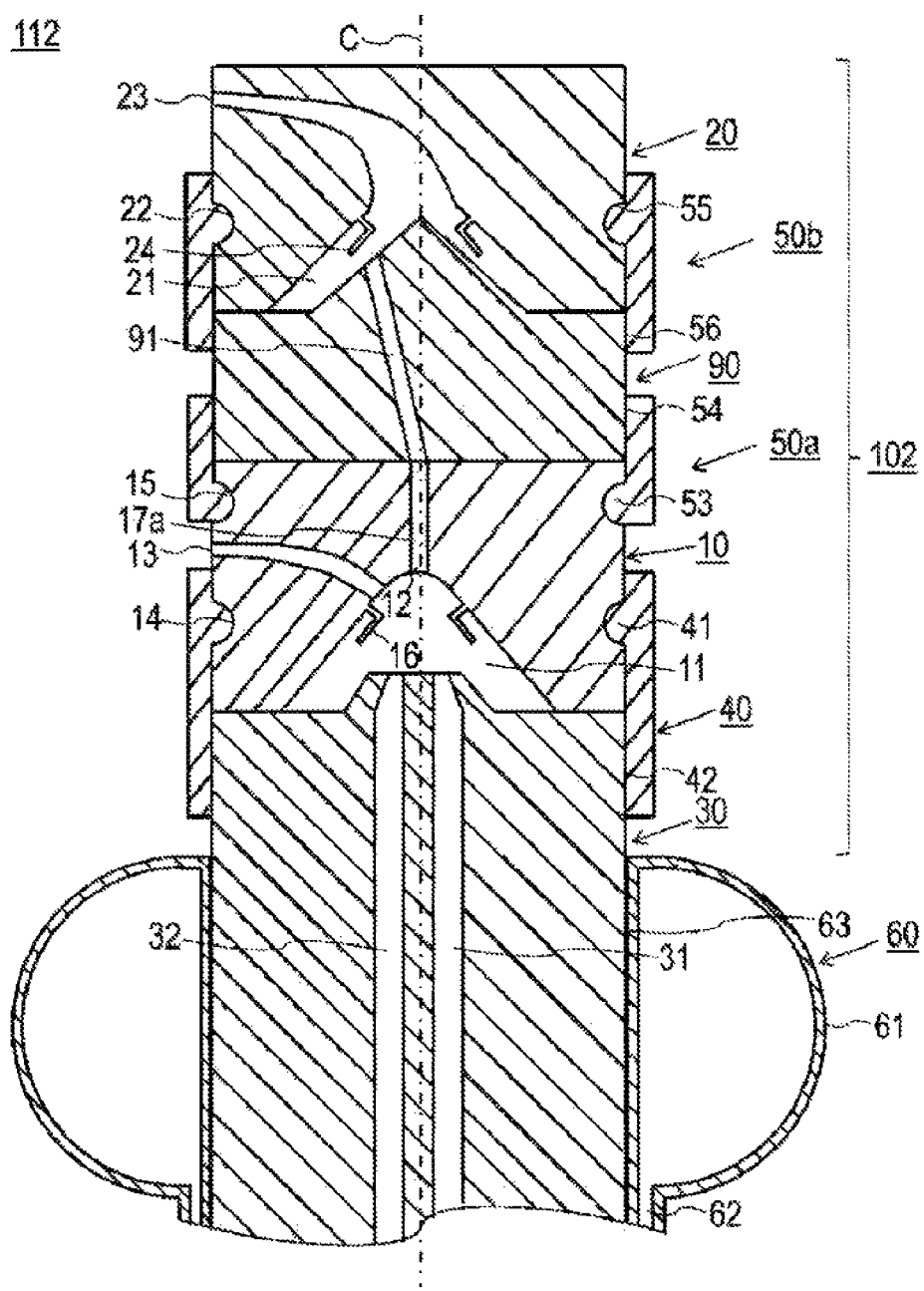
FIG. 8 is a sectional view showing a distal portion of a catheter assembly having a catheter for forming a biological tissue holding member according to a third embodiment of the present invention.

FIG. 8 is a sectional view showing a catheter assembly having a catheter for forming a biological tissue holding member according to a third embodiment; and FIG. 9 illustrates a state where the catheter assembly is inserted in a living body lumen. While a situation where a living body lumen in which to form a biological tissue holding member such as a stent has substantially linear shape has been presumed in Embodiments 1 and 2 described above, a catheter as follows may be used in the case where the body lumen is curved or bent. Note that the same configurations as those in the first embodiment above are denoted by the same reference numerals as used above, and descriptions thereof are omitted here.

A catheter 102 for forming a biological tissue holding member according to the third embodiment has a configuration in which a cylindrical opening portion lumen 17a is formed coaxially with an axis-of-rotation C of a first discharge section 10. In addition, between the first discharge section 10 and a second discharge section 20 is disposed a flexible member 90 which is flexible and is lower in rigidity than the first discharge section 10 and the second discharge section 20. The flexible member 90 is formed therein with a second space communication lumen 91 through which a mixture of curable liquid substances flowing down the opening portion lumen 17a flows into a second space 21 in the second discharge section 20.

The flexible member 90 is interlocked to the first discharge section 10 by an interlock member 50a, and is interlocked to the second discharge section 20 by an interlock member 50b. The flexible member 90 is joined at a joint part 54 of the interlock member 50a and a joint part 56 of the interlock member 50b, by welding or the like.

The interlock member 50a is provided with an engaging part 53 and the interlock member 50b is provided with an engaging part 55, whereby the first discharge section 10 and the second discharge section 20 are held rotatably. The engaging parts 53 and 55 are the same as the aforementioned engaging parts 51 and 52, and, therefore, descriptions thereof are omitted here.

Hereafter, description will be made of a procedure of forming a biological tissue holding member by use of the catheter for forming a biological tissue member according to this embodiment. First, a catheter assembly 112, with a holding balloon 60 in a deflated state, is inserted through a mouth or a nose. In the case where a body lumen part in which a biological tissue holding member is to be formed is curved as shown in FIG. 9, the structure wherein the flexible member 90 lower than the first discharge section 10 and the second discharge section 20 in rigidity is disposed between the first discharge section 10 and the second discharge section 20 ensures that the flexible member 90 is deformed in correspondence with the shape of the body lumen, and that a distal portion of the catheter 102 is curved following the curved body lumen.

When the curable liquid substances are supplied starting from this state, the first discharge section 10 possessing a first rotation driving unit 16 and the second discharge section 20 possessing a second rotation driving unit 24 discharge the mixture of the curable liquid substances while rotating, whereas the flexible member 90 possessing no rotation driving part remains non-rotating. With the catheter 102 moved along the longitudinal direction of the body lumen in the state where the first discharge section 10 and the second discharge section 20 are discharging the mixture of the curable liquid substances while rotating, it is possible to easily form a biological tissue holding member (such as a stent) which is shaped after the shape of the curved body lumen as well.

As has been described above, the catheter 102 for forming a biological tissue holding member according to the third embodiment has a structure wherein the flexible member 90 lower in rigidity than the first discharge section 10 and the second discharge section 20 is disposed between the first discharge section 10 and the second discharge section 20. The flexible member 90 is formed therein with the second space communication lumen 91 via which the opening portion lumen 17a communicates with the second space 21 in the second discharge section 20. This ensures that even where the catheter assembly 112 is inserted into a curved body lumen, the distal portion of the catheter 102 is curved along the body lumen, and the mixture of the curable liquid substances is discharged from the curved distal portion. Therefore, it is possible to easily form a biological tissue holding member which is shaped after the shape of a curved, complicated body lumen as well.

The present invention is not limited to the aforementioned embodiments, and various modifications are possible within the scope of the appended claims.

While a configuration wherein the lumens 18, 25, and 33 for passing the expansion balloon 80 therethrough are provided in central portions of the first discharge section 10, the second discharge section 20, and the main body section 30 has been described in the second embodiment above, this is not restrictive. A camera may be passed in or through the aforesaid lumens, whereby the conditions of a distal portion of the catheter during a procedure can be visually checked. This enables control of the discharge of the mixture of the curable liquid substances or the like according to the circumstances of the procedure.

DESCRIPTION OF REFERENCE SYMBOLS

10: First discharge section
100, 101, and 102: Catheter for forming a biological tissue holding member
11: First space
110, 111, and 112: Catheter assembly
12: Opening portion
13: First discharge hole
14: First engaging part
15: Second engaging part
16: First rotation driving unit
16a to 16g: First rotary vane
17 and 17a: Opening portion lumen
18, 25, and 33: Expansion balloon passing lumen (expansion passing lumen)
20: Second discharge section
21: Second space
22: Engaging part
23: Second discharge hole
24: Second rotation driving unit
24a to 24g: Second rotary vane
30: Main body section
31 and 32: Curable liquid substance lumen
40: Rotation holding section
41: Engaging part
42: Joint part
50: Interlock member
51 and 52: Engaging part
60: Holding balloon (holding catheter)
61: Balloon part
62: Holding fluid lumen
80: Expansion balloon (expansion catheter)
81: Balloon part
82: Expansion fluid lumen
83: Guide wire passing lumen

The invention claimed is:

1. A catheter for forming a biological tissue holding member, comprising:
an elongated main body section having a lumen through which can flow a curable liquid substance from a proximal end to a distal end and that is cured in a living body;

a first discharge section through which the curable liquid substance is supplied via the main body section, is configured to discharge the curable liquid substance in a filamentous form in a first direction intersecting an axial direction of the main body section;

a second discharge section which is disposed on a distal side of the first discharge section along a axial direction of the main body section as compared with the first discharge section and through which the curable liquid substance is supplied via the main body section is configured to discharge the curable liquid substance in a second direction intersecting both of the axial direction and the first direction;

a first rotation drive in communication with the first discharge section and configured to rotate the first discharge section in a first rotation direction; and a second rotation drive in communication with the second discharge section and configured to rotate the second discharge section in a second rotation direction reverse to the first rotation direction, wherein the first discharge section and second discharge section are coaxial.

2. The catheter for forming a biological tissue holding member according to claim 1, wherein the first rotation drive is provided with a first rotary vane configured to rotate the first discharge section by supply of the curable liquid substance to the first discharge section, and the second rotation drive is provided with a second rotary vane configured to rotate the second discharge section by supply of the curable liquid substance to the first discharge section.

3. The catheter for forming a biological tissue holding member according to claim 1, wherein the first discharge section is rotatably held on the main body section, and includes a first space which is disposed communicating with the lumen and into which the curable liquid substance is introduced via the lumen, an opening portion which communicates with the first space and which opens to a distal side of the first space, and a first discharge hole which communicates with the first space and through which the curable liquid substance is discharged; and the second discharge section is rotatably held on the first discharge section, and includes a second space which is disposed communicating with the opening portion and into which the curable liquid substance is introduced from the first space, and a second discharge hole which communicates with the second space and through which the curable liquid substance is discharged.

4. The catheter for forming a biological tissue holding member according to claim 3, wherein the first discharge section is provided with an opening portion lumen which extends from the opening portion and which is disposed coaxially with an axis of rotation of the first discharge section, a flexible member lower than the first discharge section and the second discharge section in rigidity is further disposed between the first discharge section and the second discharge section, and the flexible member is provided with a second space communication lumen which extends from the opening portion lumen to communicate with the second space in the second discharge section.

5. A catheter assembly comprising:

the catheter for forming a biological tissue holding member according to claim 1; and an expansion catheter provided with an expandable expansion member supporting a living body lumen to which the curable liquid substance is discharged, the supporting being conducted on a distal side as compared with the second discharge section of the catheter for discharging an embolizing matter.

6. The catheter assembly according to claim 5, further comprising an expansion passing lumen in or through which the expansion catheter is movably passed.

7. The catheter assembly according to claim 5, wherein the expansion catheter includes a balloon catheter provided with an expansion balloon as the expansion member.

8. A catheter assembly comprising:

the catheter for forming a biological tissue holding member according to claim 5; and a holding catheter provided with a catheter-passing lumen in or through which the catheter for forming a biological tissue holding member is movably passed, and with a holding balloon by which the catheter for forming a biological tissue holding member is held on a proximal side as compared with the first discharge section of the catheter for forming a biological tissue holding member while being positioned with respect to a radial direction of a living body lumen.

9. A catheter assembly comprising:

the catheter for forming a biological tissue holding member according to claim 1; and a holding catheter provided with an embolization passing lumen in or through which the catheter for discharging an embolizing matter is movably passed, and with a holding balloon by which the catheter for forming a biological tissue holding member is held on a proximal side as compared with the first discharge section of the catheter for forming a biological tissue holding member while being positioned with respect to a radial direction of a living body lumen.

10. A catheter for forming a biological tissue holding member, comprising:

an elongated main body section having a lumen through which a curable liquid can flow from a proximal end to a distal end;

a first discharge section in fluid communication with the lumen, and configured to discharge the curable liquid to a first direction intersecting a longitudinal axis direction of the elongated main body; and, a second discharge section disposed distally from the first discharge section along the longitudinal axis direction of the elongated main body section and in fluid communication with the first discharge section and the lumen, and configured to discharge the curable liquid in a second direction intersecting both the longitudinal axis direction and the first direction;

wherein the first discharge section rotates in a first rotational direction and the second discharge section rotates in a second rotational direction reverse to the first rotational direction and the first and second discharge sections are coaxial.

11. The catheter for forming a biological tissue holding member according to claim 1, further comprising, a first rotary vane disposed in the first discharge section, and a second rotary vane disposed in the second discharge section.

* * * * *